United States Patent [19]

Watson et al.

[11] 4,185,019

[45] Jan. 22, 1980

[54] PROCESS FOR PREPARING 4-PHENYL-1,3-DIOXANE

[76] Inventors: James M. Watson, 2100 Settles St.; Alan Chepregi, 1425 E. 6th St., both of Big Spring, Tex. 79720

[21] Appl. No.: 939,348

[22] Filed: Sep. 5, 1978

[51] Int. Cl.$^2$ .............................................. C07D 319/04
[52] U.S. Cl. ................................................ 260/340.7
[58] Field of Search .................................... 260/340.7

[56] References Cited

U.S. PATENT DOCUMENTS

| | | | |
|---|---|---|---|
| 2,417,548 | 3/1947 | Engel | 260/340.7 |
| 2,504,732 | 4/1950 | Rosen et al. | 260/340.7 |
| 3,414,588 | 12/1968 | Jones | 260/340.7 |
| 3,818,043 | 6/1974 | Starks | 260/340.7 |

Primary Examiner—Ethel G. Love

[57] ABSTRACT

A process for preparing 4-phenyl-1,3-dioxane from styrene and formaldehyde using a simplified method for working up the reaction mixture is disclosed, which comprises reacting styrene with an aqueous formaldehyde solution in the presence of an acidic catalyst at elevated temperatures, separating the aqueous phase from the organic phase and washing the latter with an alkaline aqueous solution to obtain a 4-phenyl-1,3-dioxane-containing product from which pure 4-phenyl-1,3-dioxane can easily be recovered, e.g., by means of distillation. The process can be further improved by adding a polymerization-inhibitor to the reaction mixture.

14 Claims, No Drawings

PROCESS FOR PREPARING 4-PHENYL-1,3-DIOXANE

BACKGROUND OF THE INVENTION

The present invention relates to a process for the industrial manufacture of 4-phenyl-1,3-dioxane from styrene, according to the general equation

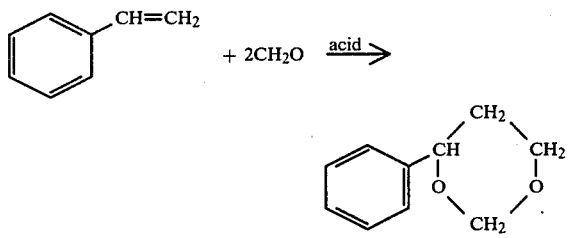

Various laboratory methods for preparing 4-phenyl-1,3-dioxane, according to the general procedure described by Prins (Chem. Weekblad 14, 932, 1917; 16, 1072 and 1510, 1919) by the reaction between styrene and formaldehyde, are known in the art (see, e.g., Organic Syntheses, Coll. Vol. IV, 786, 1963). Yet, none of the hitherto known methods are suitable for the production of 4-phenyl-1,3-dioxane on an industrial scale. The various drawbacks of the prior art methods include:

(a) the use of excessive amounts of formaldehyde;
(b) need of solvents; and
(c) extensive and uneconomical working-up for the recovery of the final product from the reaction mixture.

4-Phenyl-1,3-dioxane is a high-boiling liquid, which is useful as an industrial high-boiling solvent. It has also been reported to have utility as a plasticizer (e.g., for celluloid), curing agent (e.g., for phenolic resins), and pigment dispersant. Furthermore, it has been used, both as a monomer and as an additive, in the production of plastic polymers; in particular, it has been utilized as a component in both phenolic and styrenic systems.

SUMMARY OF THE INVENTION

It is an object of the present invention to provide a process for preparing 4-phenyl-1,3-dioxane, wherein the draw-backs of the prior art processes are avoided, and which is suitable for industrial scale production at low costs.

It is a further object of the present invention to provide such a process, which provides high yields in 4-phenyl-1,3-dioxane, relative to the starting amount of styrene.

It is a further object of the present invention to provide such a process, wherein the formation of resinous by-products is substantially eliminated.

It is a further object of the present invention to provide such a process, wherein substantially all the starting styrene is selectively converted into 4-phenyl-1,3-dioxane.

It is a further object of the present invention to provide such a process, wherein only a minimum excess of formaldehyde is required.

It is a further object of the present invention to provide such a process, which does not require extensive separating and/or purifying operations for recovering a sufficiently pure final product.

In order to accomplish the foregoing objects, according to an embodiment of the present invention, there is provided a process for preparing 4-phenyl-1,3-dioxane by reacting styrene with formaldehyde, wherein the reaction conditions are adjusted to ensure a high yield in 4-phenyl-1,3-dioxane, using a minimum amount of formaldehyde and a simplified method for recovering the 4-phenyl-1,3-dioxane from the reaction mixture. This process is consisting essentially of the steps of:

(a) subjecting a mixture comprising 1 part by mole of styrene and such an amount of an aqueous formaldehyde solution, having a formaldehyde concentration of between about 30 and about 37%, which contains from about 2 to about 2.5, preferably from about 2 to about 2.18, parts by mole of formaldehyde in the presence of an acidic catalyst, to a temperature of between about 80 and about 150° C. for a period of time sufficient to react substantially the entire amount of styrene into 4-phenyl-1,3-dioxane, whereby a reaction mixture consisting of an organic phase comprising the 4-phenyl-1,3-dioxane and an aqueous phase is obtained;

(b) separating the aqueous phase from the organic phase; ;p (c) washing the organic phase with an aqueous alkaline solution to obtain a crude 4-phenyl-1,3-dioxane-containing product; and (d) recovering the 4-phenyl-1,3-dioxane from the crude product.

Furthermore, it has been found that in the preparation of a process for preparing 4-phenyl-1,3-dioxane from styrene and formaldehyde by the foregoing procedure, the yield in 4-phenyl-1,3-dioxane can be increased and its stability can be favorably influenced if a polymerization-inhibitor is incorporated into the styrene- and formaldehyde-containing mixture. Thus, according to another embodiment of the present invention, there is further provided a process for preparing 4-phenyl-1,3-dioxane, which comprises the step of reacting styrene with a formaldehyde-generating agent selected from the group consisting of an aqueous formaldehyde solution and paraformaldehyde in the presence of an acidic catalyst and a polymerization-inhibitor, in particular a dinitrophenol derivative.

If the polymerization-inhibitor is a dinitrocresol, the latter simultaneously can serve as a reaction-end-point indicator by means of which substantial completion of the reaction is indicated by a change in color of the reaction medium.

Further objects, features, and advantages of the present invention will become apparent from the detailed description of the invention, which follows.

DETAILED DESCRIPTION OF THE INVENTION

According to an embodiment of the present invention, there is provided a process for preparing 4-phenyl-1,3-dioxane by reacting styrene in the presence of an acidic catalyst with a concentrated aqueous formalin solution (formaldehyde content between about 30 and 37%), whereby, contrary to conventional methods, such a low amount of formalin solution is used that any substantial excess of formaldehyde is avoided. The molar ratio formaldehyde/styrene is between about 2.00 and about 2.50, preferably between about 2.00 and about 2.18. The reaction temperature in this process is between about 80° and about 150° C., preferably between about 90° and 125° C., in particular about 100° C. Depending on the specific reaction temperature, the reaction period may vary. At a reaction temperature of between about 100° and about 120° C., reaction periods of several hours, e.g., from about 4 to about 10 hours, are suitable.

As acidic agents within the process, according to the present invention, there may be used strong mineral acids, such as $H_2SO_4$, $H_3PO_4$, or HCl; strong organic acids, e.g., arylsulfonic acids, ion-exchange resins. Strong mineral acids, in particular $H_2SO_4$, especially aqueous sulfuric acid solutions containing from about 25 to about 35% of $H_2SO_4$, are preferred.

Unexpectedly, it has been found that even though no substantial excess of formaldehyde is applied in the process according to the present invention, the degree of conversion of the styrene into 4-phenyl-1,3-dioxane is very high.

Furthermore it has, surprisingly, been found, that the 4-phenyl-1,3-dioxane can readily be recovered in high yields and with a high degree of purity from the reaction mixture which is obtained under the reaction conditions, as defined in the present process. The resulting reaction mixture readily separates into an organic phase comprising the 4-phenyl-1,3-dioxane, and a supernatant aqueous phase which can easily be separated therefrom by mere decantation.

After washing the raw organic phase with an alkaline aqueous solution, preferably a sodium hydroxide solution, which includes sufficient alkali to neutralize the product and/or remove residues of the acidic catalyst therein, a crude 4-phenyl-1,3-dioxane-containing product is obtained, from which the 4-phenyl-1,3-dioxane can be recovered in sufficiently pure form by distillation without requiring any additional isolation-and/or purification procedures. The distillation may be carried out under reduced pressure or under ambient atmospheric pressure, and the distillation temperature of course will vary, depending on the distillation pressure. At a reduced pressure of from about 12 to about 15 mm Hg, the distillation temperature suitably is between about 125° and about 135° C.

It has further been found that the storage stability of the crude 4-phenyl-1,3-dioxane-containing product as well as of the final pure 4-phenyl-1,3-dioxane can be largely increased, and peroxide formation during storage can be substantially prevented, if the product is stored under wet caustic conditions, e.g., if the product is in intimate contact with a peroxide-formation-inhibiting amount of an alkali-containing aqueous solution, such as an aqueous alkali-hydroxide solution. According to a preferred embodiment of the present invention, a storage-stable crude 4-phenyl-1,3-dioxane product is obtained in step (c) of the present process by retaining a residual amount of the alkaline washing solution in the crude product as at least part of the alkali-containing aqueous solution.

It has also been found that in a process for preparing 4-phenyl-1,3-dioxane by reacting styrene with formaldehyde in the presence of an acidic catalyst, the yield in 4-phenyl-1,3-dioxane can be increased and the formation of resinous by-products, which impede the recovery and/or purification of the product, can be largely reduced independently from the specific process conditions, if a polymerization-inhibitor is present in the reaction mixture. Any radical scavengers which are conventionally used as polymerization inhibitors in connection with styrene and styrene polymerization processes can be used within the process according to the present invention. Suitably, such polymerization-inhibitors include hydroquinones, quinones, or phenols, which may be mono- or poly-substituted by lower alkyl, lower alkoxy, amino or nitro, and aromatic nitroso- or nitro-compounds, such as mono- or dinitro-substituted benzenes, phenols, or anilines, or mononitroso anilines. Most preferred are dinitrophenols and lower alkyl- or lower alkoxy substituted dinitrophenols, such as 2,6-dinitrophenol, 2,4-dinitro-o-cresol and, in particular, 2,6-dinitro-p-cresol.

It has further been found that if dinitrocresols, in particular 2,6-dinitro-para-cresol, are added to the reaction mixture as a polymerization-inhibitor, the latter acts as a reaction-end-point indicating agent and the reaction mixture undergoes a change in color when the reaction is substantially completed. Thus, according to the present invention there is also provided a convenient method for indicating the substantial completion of the reaction and determining the length of time during which the reaction mixture should be heated. By using a dinitrocresol for indicating substantial completion of the 4-phenyl-1,3-dioxane formation, any excessive heating of the reaction mixture, which might lead to the formation of undesirable by-products, can be avoided.

The amount of polymerization-inhibitor may vary, depending on the specific type of inhibitor used. In the case of dinitrophenols and substituted dinitrophenols, amounts of between about 100 and about 1000 ppm relative to the amount of styrene, are suitable, whereby amounts from about 400 to about 500 ppm are preferred.

Any process for preparing 4-phenyl-1,3-dioxane can be improved according to the present invention by adding a polymerization-inhibitor to the starting styrene- and formaldehyde-containing reaction mixture, regardless of whether any conventional process- and working-up-conditions are used, or whether the process according to the above described embodiment of the present invention is used.

According to a particularly preferred embodiment of the present invention, a polymerization-inhibitor, in particular a dinitrophenol derivative, such as 2,6-dinitro-p-cresol, is added to the mixture in step a) of the process according to the embodiment of the present invention defined on page 3.

This invention will be further illustrated by the following non-limiting working examples.

EXAMPLE 1

A mixture of 1 part by mole of styrene, an amount of a 37% formalin solution containing 2.17 parts by mole of formaldehyde, and an amount of an aqueous approximately 30% sulfuric acid solution containing 0.08–0.1 moles of $H_2SO_4$ is kept at a temperature of 100° C. for a period of 8 hours under agitation. Subsequently, the reaction mixture is cooled and is allowed to settle. The supernatant aqueous phase is decanted from the organic phase which has gathered on the bottom of the reactor. Then the organic phase is sufficiently washed with an 0.1 molar solution of sodium hydroxide to neutralize any acidic components therein. After separation from the washing solution, the raw organic phase is directly subjected to distillation under reduced pressure of 12–15 mm Hg at a temperature of 125°–135° C.

From the analytical data of the obtained distillate product which are given below, it is apparent that the distillate consists of 4-phenyl-1,3-dioxane of a satisfactory degree of purity.

| Elemental Analysis: | Calc. | C=73.15 | H=7.37 | O=19.49 |

| | | | |
|---|---|---|---|
| Found | 73.45 | 7.34 | 19.42 |
| Duplicate | 73.55 | 7.55 | 19.37 |

TLC: Thin layer chromatography, using a variety of absorbents, fails to find more than one major component.

IR: Infrared spectrum is consistent with structure of 4-phenyl-1,3-dioxane, no bands present which could be assigned to oxygen except as ether linkages (OH, carbonyl, carboxyl absent), no evidence of active unsaturation. Strong bonds at 705, 760, 980, 1030, 1095, 1120, 1180, 1250, 1380, 1460 cm$^{-1}$.

B.P.: Consistent with literature.* Furthermore, fractionation of simple distillates provides absolutely flat temperature profile between 10–90% distillation.

$N_D^{20}$: Consistent with literature.*
Literature value 1.5300–1.5311
Actually found value 1.5301

$d_4^{20}$: Consistent with literature.*
Literature value 1.092–1.093
Actually found value 1.092 at 22° C.

* Org. Syn. Coll. Vol. IV, 786 (1963).

EXAMPLE 2

A mixture of 468 g of styrene, 790.5 g of 37% formalin solution, and 20 g of concentrated sulfuric acid is maintained at a temperature of 100° C. for a period of 5 hours and subsequently at a temperature of 120° C. for a period of 3 hours. Subsequently, the reaction mixture is worked up as described in Example 1.

RESULTS:

| | |
|---|---|
| Amount of reacted styrene | 97.5% |
| Weight of the crude organic phase | 730.0 g |
| Weight of the distillate heart cut | 613.5 g |
| Weight of the distillation residue | 54.0 g |
| The distillation residue is a semi-solid product. | |

EXAMPLE 3

The process as described in Example 2 is repeated, yet 0.2 g of 2,6-dinitro-p-cresol are added to the mixture. At the end of the reaction, the reaction mixture turns fuchsia.

RESULTS:

| | |
|---|---|
| Amount of reacted styrene | 95.9% |
| Weight of crude organic phase | 718.5 g |
| Weight of distillate heart cut | 615.0 g |
| Weight of distillation residue | 29.5 g |

The distillation residue is a liquid of low viscosity. Comparing the amounts and the consistency of the distillation residue which are obtained in Examples 2 and 3, it is apparent that the formation of resinous byproducts under consumption of styrene is reduced by about 40% in the presence of 2,6-dinitro-p-cresol.

What is claimed is:

1. A process for preparing 4-phenyl-1,3-dioxane, consisting essentially of the steps of:

(a) subjecting a mixture comprising 1 part by mole of styrene a polymerization inhibitor and such an amount of an aqueous formaldehyde solution, having a formaldehyde concentration of between about 30 and about 37%, which contains from about 2 to about 2.5 parts by mole of formaldehyde in the presence of an acidic catalyst, to a temperature of between about 80° and about 150° C. for a period of time sufficient to react substantially the entire amount of styrene into 4-phenyl-1,3-dioxane, whereby a reaction mixture consisting of an organic phase comprising the 4-phenyl-1,3-dioxane and an aqueous phase is obtained;

(b) separating the aqueous phase from the organic phase;

(c) washing the organic phase with an aqueous alkaline solution to obtain a crude 4-phenyl-1,3-dioxane-containing product; and (d) recovering the 4-phenyl-1,3-dioxane from the crude product.

2. The process as defined in claim 1, wherein the polymerization inhibitor is selected from the group consisting of hydroquinones, quinones, phenols, and nitro-substituted aromatics.

3. The process as defined in claim 2, wherein the polymerization-inhibitor is a dinitrophenol or a lower alkyl-substituted dinitrophenol.

4. The process as defined in claim 3, wherein the mixture comprises a reaction-end-point-indicating polymerization-inhibitor which is a dinitrocresol, and wherein substantial completion of step a) is indicated by a change in color of the reaction mixture.

5. The process as defined in claim 4, wherein the polymerization-inhibitor is 2,6-dinitro-para-cresol.

6. A process for preparing 4-phenyl-1,3-dioxane which comprises the step of reacting styrene with a formaldehyde generating agent selected from the group consisting of an aqueous formaldehyde solution and paraformaldehyde in the presence of an acidic catalyst and a polymerization-inhibitor.

7. The process as defined in claim 6, wherein the polymerization-inhibitor is selected from the group consisting of hydroquinones, quinones, phenols, and nitro-substituted aromatics.

8. The process as defined in claim 7, wherein the polymerization-inhibitor is a dinitrophenol or a lower alkyl-substituted dinitrophenol.

9. The process as defined in claim 6, wherein the acidic catalyst is a mineral acid.

10. The process as defined in claim 9, wherein the mineral acid is sulfuric acid.

11. The process as defined in claim 10, wherein the acidic catalyst is an aqueous sulfuric acid solution, containing between about 25 and 35% of sulfuric acid.

12. The process as defined in claim 8, wherein the polymerization-inhibitor is a dinitrocreseol and substantial completion of the reaction is indicated by a change in color.

13. The process as defined in claim 12, wherein the polymerization-inhibitor is 2,6-dinitro-para-cresol.

14. A 4-phenyl-1,3-dioxane composition comprising 4-phenyl-1,3-dioxane and a peroxide-formation-inhibiting amount of an alkali-containing aqueous solution.

* * * * *